(12) United States Patent
Chen et al.

(10) Patent No.: US 7,345,256 B2
(45) Date of Patent: Mar. 18, 2008

(54) METHODS AND APPARATUS FOR DELIVERING LASER ENERGY FOR JOINING PARTS

(75) Inventors: Ziyun Chen, 13625 Tradition St., San Diego, CA (US) 92128; Ping Ye Zhang, 11865 Aspen View Dr., San Diego, CA (US) 92128

(73) Assignees: Ziyun Chen, San Diego, CA (US); Ping Ye Zhang, San Diego, CA (US)

( * ) Notice: Subject to any disclaimer, the term of this patent is extended or adjusted under 35 U.S.C. 154(b) by 0 days.

(21) Appl. No.: 11/093,331

(22) Filed: Mar. 29, 2005

(65) Prior Publication Data

US 2005/0224471 A1   Oct. 13, 2005

Related U.S. Application Data

(60) Provisional application No. 60/560,349, filed on Apr. 8, 2004.

(51) Int. Cl.
*B23K 26/00* (2006.01)
(52) U.S. Cl. .............................. 219/121.6; 219/121.64; 219/121.85
(58) Field of Classification Search ............. 219/121.6, 219/121.64, 121.63, 121.66, 121.65, 121.85, 219/121.86, 61, 60 A, 60.2, 159, 160
See application file for complete search history.

(56) References Cited

U.S. PATENT DOCUMENTS

| | | | | |
|---|---|---|---|---|
| 4,069,080 A | * | 1/1978 | Osborne | 156/272.8 |
| 4,528,436 A | * | 7/1985 | Stol | 219/74 |
| 4,577,088 A | * | 3/1986 | Sharp | 219/121.63 |
| 4,633,870 A | * | 1/1987 | Sauer | 606/8 |
| 4,990,139 A | * | 2/1991 | Jang | 604/101.01 |
| 5,152,855 A | * | 10/1992 | Jansman et al. | 156/73.5 |
| 5,387,211 A | * | 2/1995 | Saadatmanesh et al. | 606/10 |
| 5,407,119 A | * | 4/1995 | Churchill et al. | 228/124.5 |
| 5,501,759 A | * | 3/1996 | Forman | 156/272.8 |
| 5,715,375 A | * | 2/1998 | Ito et al. | 700/258 |
| 6,139,525 A | * | 10/2000 | Davis-Lemessy et al. | 604/103 |
| 6,278,079 B1 | * | 8/2001 | McIntyre et al. | 219/121.67 |
| 6,409,863 B1 | * | 6/2002 | Williams et al. | 156/198 |
| 6,740,191 B2 | * | 5/2004 | Clarke et al. | 156/272.8 |
| 6,742,236 B1 | * | 6/2004 | Dion et al. | 29/434 |
| 6,763,045 B2 | * | 7/2004 | Hastings | 372/24 |
| 2003/0141002 A1 | * | 7/2003 | Flanagan | 156/64 |
| 2004/0249277 A1 | * | 12/2004 | Kato et al. | 600/434 |

FOREIGN PATENT DOCUMENTS

BE   1002911 A  *  7/1991

\* cited by examiner

*Primary Examiner*—M. Alexandra Elve
(74) *Attorney, Agent, or Firm*—Duckor Spradling Metzger & Wynne; Bernard L. Kleinke

(57) ABSTRACT

A method and apparatus for bonding a pair of tubular members are disclosed. First and second end portions of the tubular members are gripped for rotation about their axis. The tubular members are axially rotated and a laser beam is directed radially toward the tubular members to bond them together.

14 Claims, 7 Drawing Sheets

METHODS AND APPARATUS FOR DELIVERING LASER ENERGY FOR JOINING PARTS

RELATED APPLICATION

The present application claims priority to U.S. provisional patent application, entitled METHODS AND APPARATUS FOR DELIVERING LASER ENERGY FOR JOINING PARTS, assigned application No. 60/560,349, and filed Apr. 8, 2004.

FIELD OF THE INVENTION

The present invention relates in general to the field of methods and apparatus to deliver laser energy for joining piece parts composed of materials such as plastic, metal or others. More particularly, the invention relates to joining centric tubular members, such as portions of angioplasty balloon catheters.

DESCRIPTION OF RELATED ART

This section describes the background of the disclosed embodiment of the present invention. There is no intention, either express or implied, that the background art discussed in this section legally constitutes prior art.

Laser bonding has been successfully utilized in a number of applications to provide welding of piece parts. U.S. Pat. No. 4,990,741 entitled "Method of Laser Welding" is directed towards welding first and second metallic components along a bond path, with the coherent electromagnetic energy laser beam focused by a low turbulent flow of an inert shielding gas along a portion of the path. The laser beam is provided by a continuous wave carbon dioxide laser and has a power of at least approximately 1000 watts. The laser beam welds together parts with thicknesses in the range of approximately 0.02 inch to 0.1 inch. One shortcoming of this welding approach may be that the laser beam may be too powerful to weld thin parts, i.e. part thickness in the range of 0.01 inch or thinner for some applications. Since the energy of the laser beam may be distributed in a weld zone of approximately 0.03 inch wide and 0.5 inch long, another limitation of this welding approach may be that it is not able to form a narrow weld, i.e. weld width shorter than 0.5 mm for some applications.

In U.S. Pat. No. 3,974,016, filed by Bondybey, et al., a method to bond cylindrical strands with plastic jackets using laser energy was disclosed. More specifically, the method discloses a process of bonding wire cables and fiber glass cables with plastic jackets using laser energy.

Methods for bonding plastic parts using laser energy were disclosed in U.S. Pat. No. 4,069,080 and U.S. Pat. No. 6,465,757. The methods were used in bonding plastic sheets and films and did not address the issues involved in bonding tubular plastic objects.

The patents addressing the bonding of tubular plastic parts using laser energy are U.S. Pat. Nos. 5,267,959 and 5,501,759 both entitled "Laser Bonding of Angioplasty Balloon Catheters." These patents disclose a method for forming a narrow heat fusion bond between polymeric tubular parts that are specifically used for angioplasty catheters. The bond is created by using monochromatic laser energy at a wavelength selected to at least approximately match a wavelength of maximum spectral absorption of the polymeric materials.

BRIEF DESCRIPTION OF THE DRAWINGS

The features of this invention and the manner of attaining them will become apparent, and the invention itself will be best understood by reference to the following description of certain embodiments of the invention taken in conjunction with the accompanying drawings, wherein.

DETAILED DESCRIPTION OF CERTAIN EMBODIMENTS OF THE INVENTION

Figure 1:
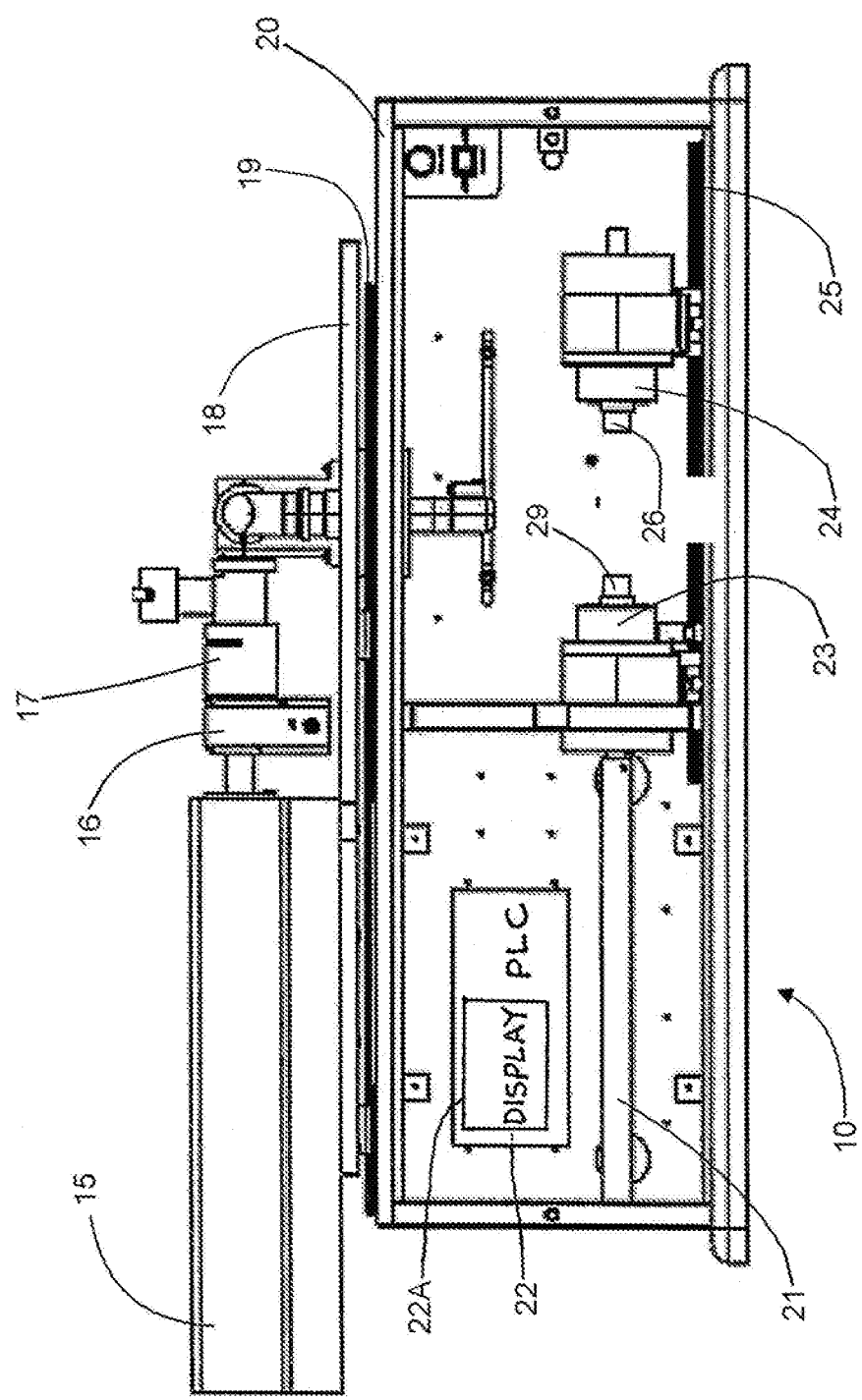
FIG. 1 is an elevational view of a laser welding apparatus, which is constructed according to an embodiment of the invention.

It will be readily understood that the components of the embodiments as generally described and illustrated in the drawings herein, could be arranged and designed in a wide variety of different configurations. Thus, the following more detailed description of the embodiments of the system, components and method of the present invention, as represented in the drawings, is not intended to limit the scope of the invention, as claimed, but is merely representative of the embodiments of the invention.

A method and apparatus for bonding a pair of tubular members are disclosed. First and second end portions of the tubular members are gripped for rotation about their axis. The tubular members are axially rotated and a laser beam is directed radially toward the tubular members to bond them together.

According to another embodiment of the invention, the laser beam can be moved axially relative to the rotating tubular members to achieve a desired bonding characteristics.

According to further embodiments of the invention, there is provided a method and apparatus for delivering laser beams with wave lengths selectively to the rotating members to be joined.

The embodiments of the present invention relates to the field of methods and apparatus which are well suited for delivering laser energy to bond and/or shape tubular parts (plastic or metal, for example).

In one embodiment, the apparatus may include at least one laser generator which is the power source to heat tubular piece parts to be bonded and/or shaped. The laser may be of type CO2, YAG, Excimer, or diode laser, with wave length in the range of 300 nm to 15 μm. Particularly, multiple laser generators with different wavelengths may be combined to provide wide coverage of various types of polymers, polymer blends, and polymers with specially formulated coating of absorbing agents. In an embodiment where multiple laser generators are used, a beam combiner for each generator may be used to introduce the beam into the main laser beam. In addition, the wave length for each laser generator may be independently adjustable. For such a multi-generator arid multi-wavelength system, the final laser beam may contain only one monochromatic beam or combinations of multiple wavelengths.

According to other embodiments, the apparatus may include at least one beam delivery system which shapes and focuses the laser beam generated by the laser generator and delivers the laser beam to the predetermined location. In accordance with one preferred embodiment of the present invention, the laser beam system may include a lower power diode laser pointer to guide the laser beam; a set of beam path enclosure tubes to prevent operators from accessing the laser beam; one or more mirror block or blocks should it be necessary or important to change the direction of the laser beam; a beam expander to enlarge the beam waist, collimator to make the enlarged beam parallel, and an integral focus lens to shape and focus the collimated laser beam at the predetermined location. Such beam delivery system may allow easy adjustment for laser beam spot size and laser beam focus distance for various piece parts bonding/shaping applications. Of particular interest, cylindrical focus lens may be used to create focused laser line instead of spot.

The laser system motion hardware may move the laser system at one or more directions so that bonding/shaping may be formed in certain patterns. In an exemplary embodiment of the present invention, the laser system motion hardware may include a moving plate, at least one linear actuator that drives the moving plate, a base plate, at least one rail placed between the moving plate and the base plate. The moving plate may situate the laser generator and laser beam delivery system in place and may move at predetermined directions, speeds and travel distances. The rails may be aligned so that single-axis or multi-axis movement of the laser system may be created.

The rotational fixtures of the apparatus of an embodiment of the invention may hold the samples to be bonded in place and rotate the samples to create circumferential welds. The rotational fixtures may include left and right spindles that rotate at the same speed. Each spindle may include a hollowed shaft that may allow long samples to run through, a sample holder that may hold and rotate the samples without damaging them, and a motor that drives the spindle. The rotational motion of the spindles may be continuous or it may be intermittent. The intermittent motion may be used to create non-continuous patterned circumferential bond.

According to an embodiment of the invention, the apparatus may include a safety enclosure which may be a fixture including one or more chambers with electrical, mechanical, and optical components enclosed inside.

According to an embodiment, there is provided a process monitoring system for on-line process monitoring. It may include a digital camera, a high resolution monitor, a lens system, and a camera mounting system.

According to other embodiments, a control system hardware may include hardware support for the laser apparatus to fulfill its functionality. It may include a PLC (program logic controller), DC power supplies, motor driver(s), laser control circuitry, operator interface including control panels and appropriate LCD displays. The control system software may be a software program run on the PLC that controls all the activities of the laser bonder.

In one preferred embodiment, the laser bonder may be programmed to run in a manual mode, a static mode, a dynamic mode and a multi-step mode. In manual mode, the laser beam power density and spindle rotational speed may be pre-specified. The apparatus of the present embodiment may enable users to manually control the laser beam movement and laser beam duration time. The manual mode may be useful for welding/reshaping process exploration. In static mode, the laser beam power density, laser beam duration, and spindle rotation speed may be pre specified. Laser beam may be directed onto the desired location without movement. This type of program may be useful for creating a smallest possible, or at least greatly reduced, welding zone. In dynamic mode, the laser beam power density, laser beam travel distance, laser beam travel speed, and spindle rotation speed may be pre-specified. The laser beam may emit while traveling, which may create extended welding areas or help reshape piece parts such as tip tapering. The multi-step mode may be a combination of static and dynamic modes. With a multi-step program, a simple welding/reshaping process may be developed with accuracy for various welding applications.

The embodiments of the invention may also provide methods of welding and/or shaping piece parts. In one preferred embodiment, the method may include the steps of: a) placing piece parts to be welded or shaped into rotation fixtures; b) positioning the laser pointer to the to be welded or to be reshaped site; c) adjusting laser beam focus distance, laser beam spot size for different piece part materials and dimensions, to achieve desired welding dimensions and welding strength; d) rotating the piece parts as needed in predetermined rotation speed to achieve annular welding zone; e) selecting creating laser bonding program; and f) starting the laser beam to the desired location to start a welding or reshaping process.

Figure 2:
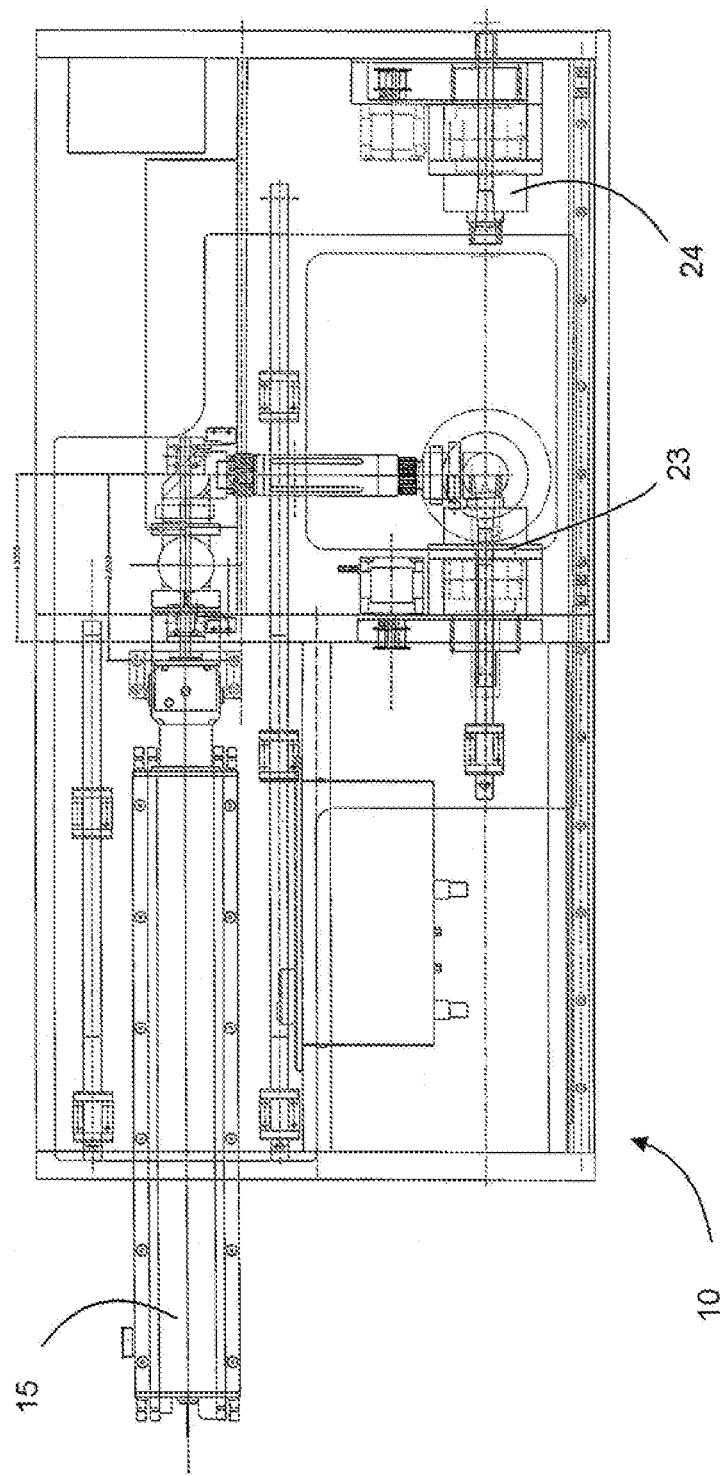
FIG. 2 is a plan view of the apparatus of FIG. 1.

Referring now to the drawings, FIG. 1 and FIG. 2 are the front and top views of a laser welding apparatus 10 of an embodiment of the present invention with a single laser generator 15, the diode pointer 16, and the laser beam delivery system 17 are resting on and supported by a moving plate 18 which in turn is mounted for movement on two or more rails 19. The entire laser system including the moving plate and the mechanical rails are mounted on top of a safety enclosure 20. Inside the enclosure, there is a left spindle 23 and a right spindle 24. The left spindle is extended with a hollow shaft 21 for long sample support. Both the left and the right spindles may be mounted for movement along a mechanical rail 25. The right spindle may be moved adjustably left and right along the rail.

A control system hardware includes a programmable logic controller (PLC) 22 with at least two channels of stepper motion control outputs. A LCD display 22A that serves as a main machine interface allows the user to program the laser bonder and to acquire operating information. A control system software is a set of ladder logic program codes may provide the following four types of programs; a) manual bonding in which the percent of laser power and sample rotational speed are preset, while the bonding duration and laser movement is controlled manually by the operator; b) static bonding with which the laser system does not move during bonding. In this type of programs, the percentage of laser power, the rotational speed, and the bonding duration must be preset; c) dynamic bonding with which the laser system is moving while laser is firing, in the type of programs, the percentage of laser power, the rotational speed, the laser travel speed and travel distance must be preset; and d) multi-step bonding which is a combination of static and dynamic bonding programs.

Figure 5:
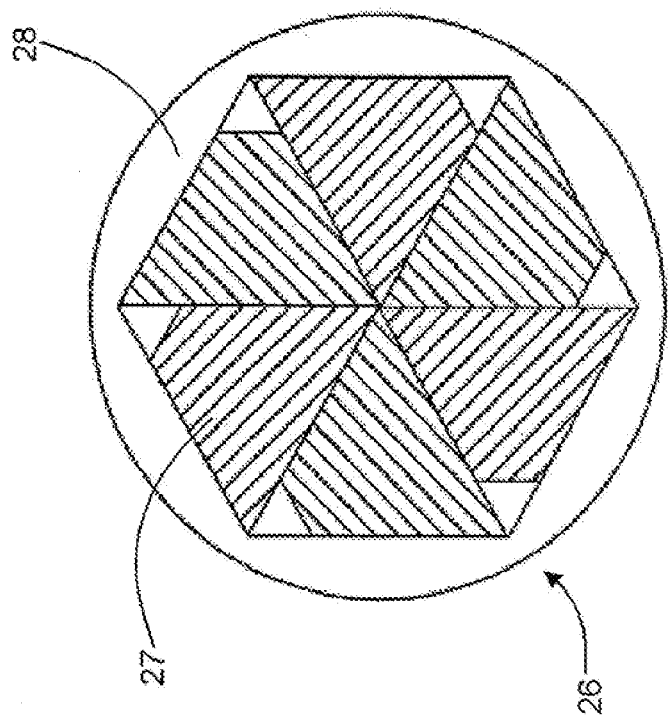
FIG. 5 is an enlarged face view of the collet of FIG. 4, illustrating it in a fully closed position.
Figure 4:
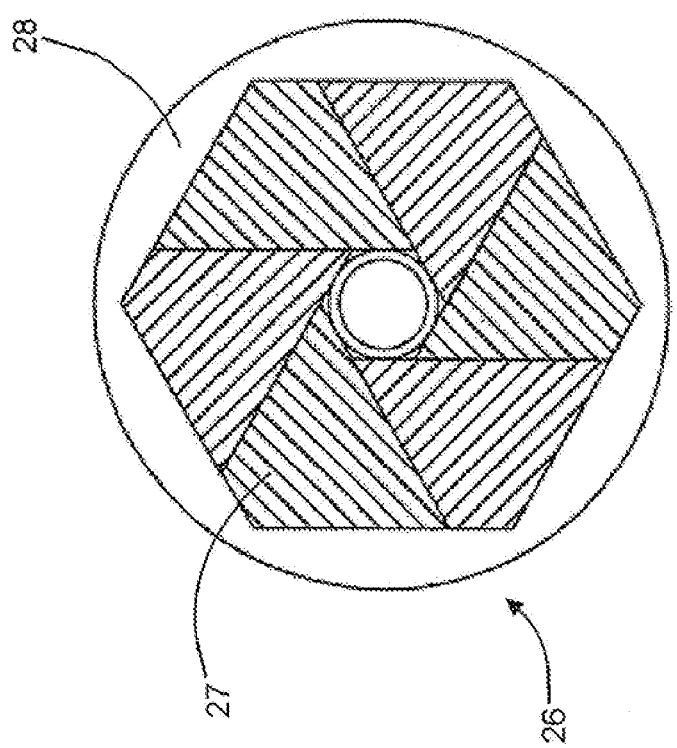
FIG. 4 is an enlarged face view of a collet of the apparatus of FIG. 1, illustrating it in a tube clamping position.

FIG. 5 is a multi-segmented collet 26 forming a part of the spindle 24, the spindle 23 having a similar collet 29 (FIG. 1). Each collet has three or more identical segments such as a segment 27. The segments are fit into a polygon housing 28 that allows the segments to move along each side of housing. As a result, the opening formed by the inner sides of the segments may be adjusted continuously. This is superior to the collet system used in machine tools in that the collet system in the current invention does not have any gap between segments. This eliminates the possibility of pinching the tubing that may be trapped in the gap. It also may have the advantage of providing a larger adjusting range for the opening.

Figure 6:
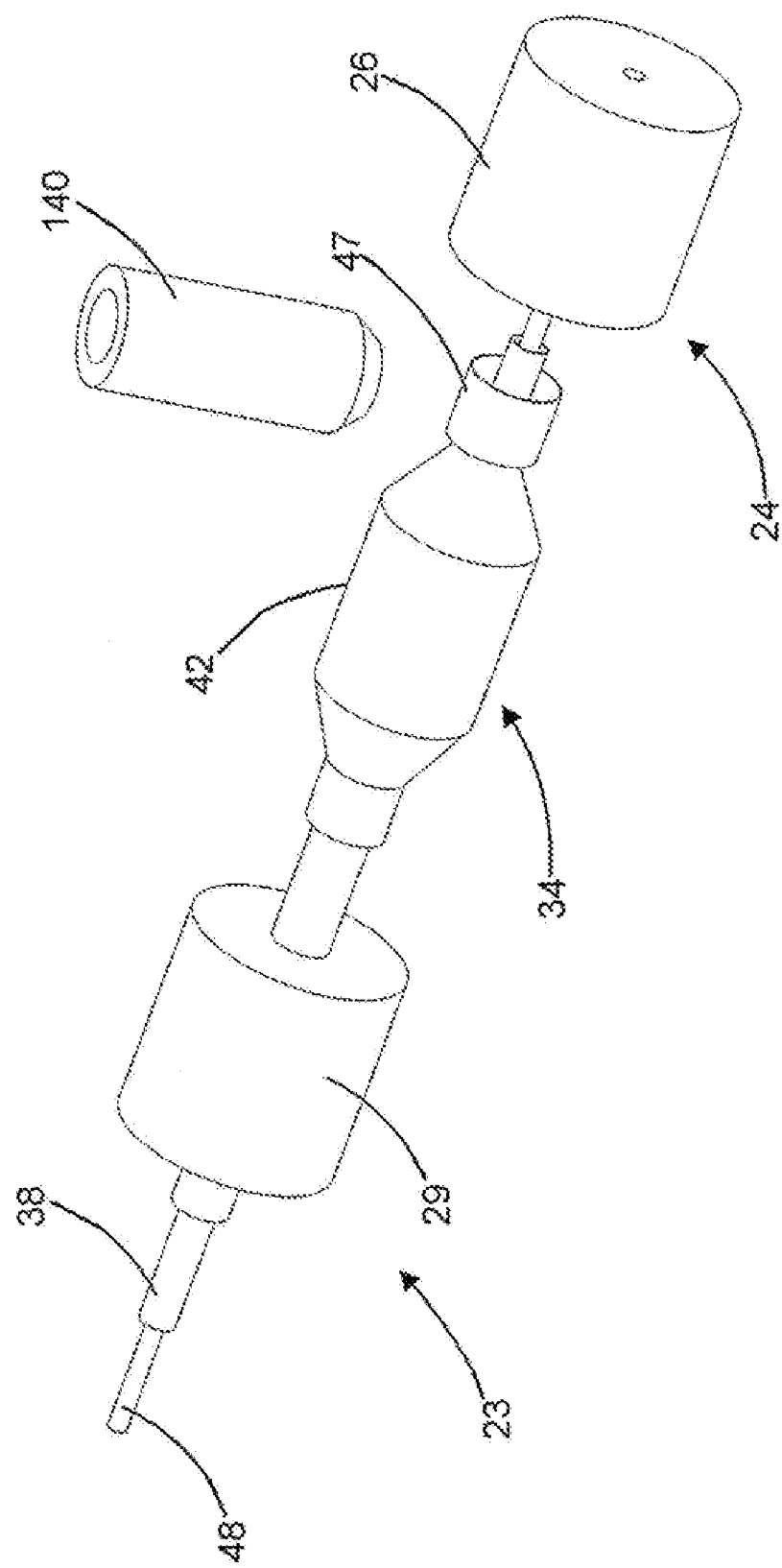
FIG. 6 is a pictorial view of the laser welding components of the apparatus of FIG. 1.
Figure 7:
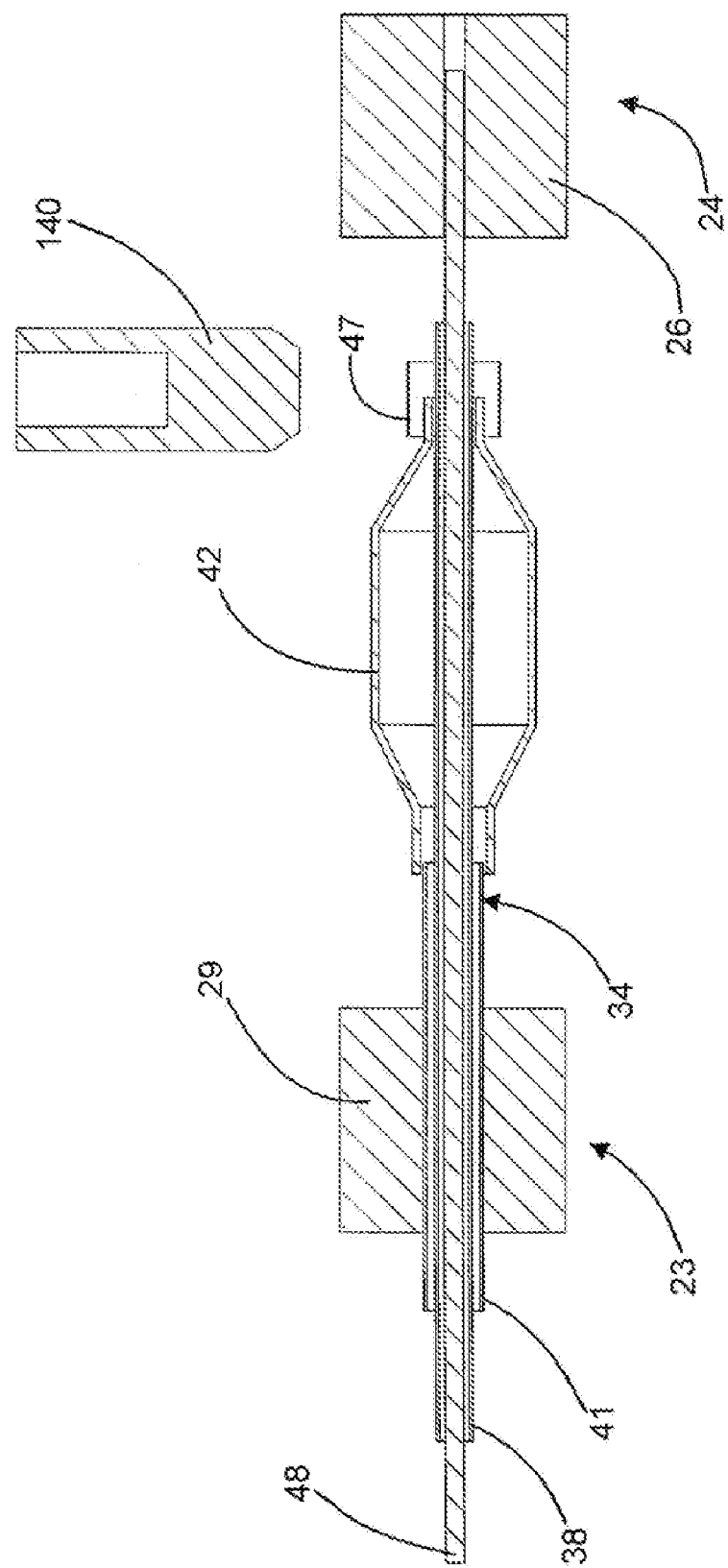
FIG. 7 is a sectional view of the components of FIG. 6.

Referring now to FIGS. 6 and 7 on the drawings, a balloon catheter 34 is supported between the collets 26 and 29. The catheter includes a catheter tubing 38 and a dilation balloon 42 concentrically surrounding the catheter tubing 38 with a tubular member 41 interposed between the proximate end of the balloon 42 and the catheter tubing 38. A shrink tube 47 loosely surrounds the distal or tip of the balloon 42 and the catheter tubing 38.

A mandral 48 extends through the interior of the catheter tubing 38, and its right hand end is gripped in the collet 26. The collet 29 grips the combination of the tubular member 41, the catheter tubing 38 and the mandral 48. The collets 26 and 29 are driven into rotation at the same speed in synchronism to cause the catheter 34 to rotate about its axis as the laser beam is emitted from the focus lens 140 onto the shrink tube 47. Thus, the catheter is securely held in place as it rotates axially to help provide a precise weld between the distal end of the balloon 42 and the distal end of the inner catheter tubing 38.

In accordance with an embodiment of the invention, the laser system including the focus lens 140 is adapted to move in a direction generally parallel to the axis of the catheter 34 as it rotates to provide for different desired welding or shaping operations.

Figure 3:
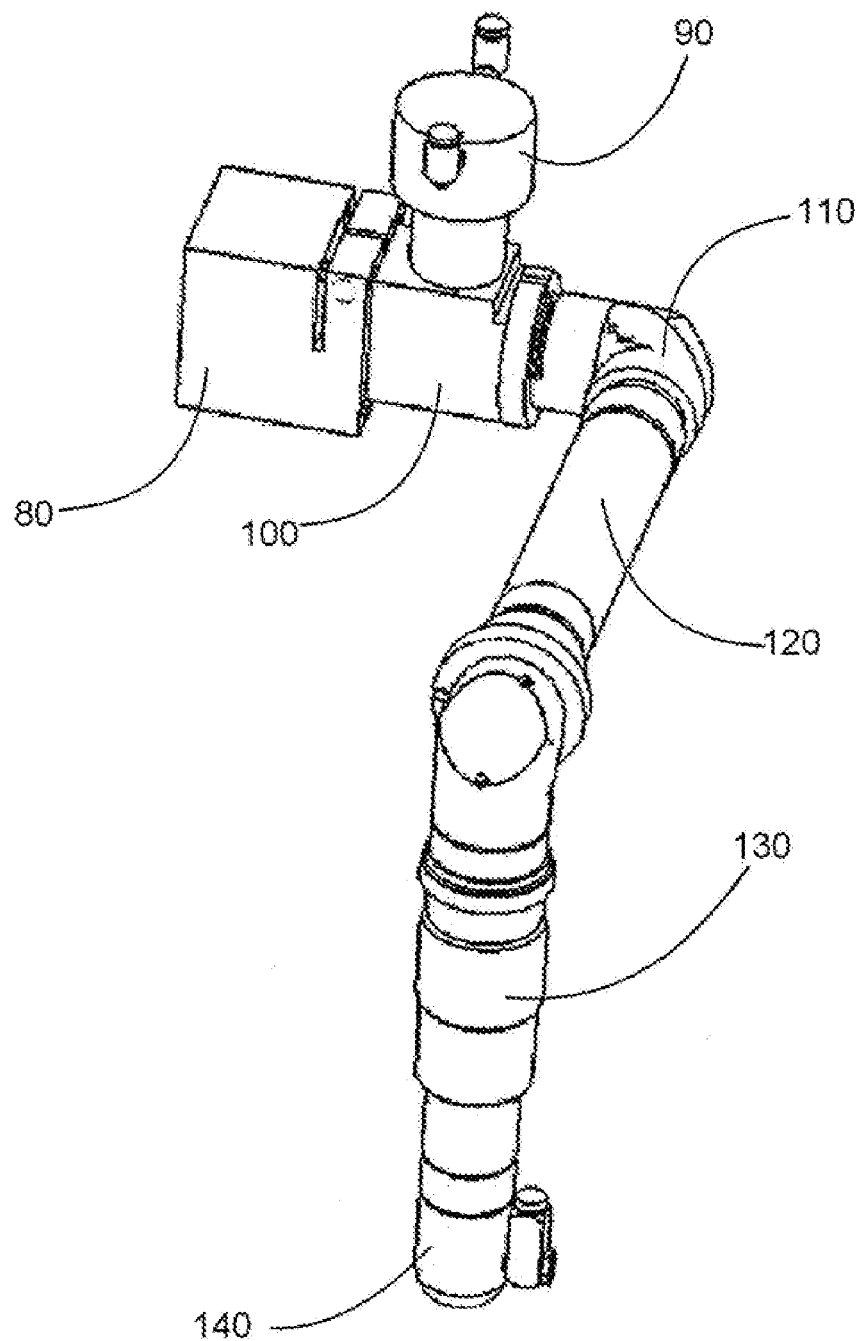
FIG. 3 is an enlarged pictorial view of a laser generator of the apparatus of FIG. 1.

FIG. 3 is a 3D view of a laser beam delivery system 15 utilized in the present invention. It consists of a mounting block 80, a beam dump 90, a beam splitter 100, one or more beam benders 110, a collimator 120, an adjustable spacer 130, and pre-mounted focus lens 14. In this particular arrangement, the beam splitter 100 splits the main laser beam into two portions. One portion travels forward along the main beam path and towards the bonding site. The other portion is branched off the main laser beam and is directed to the beam dump. The percentage of the dumped portion is between about 50% and about 90%. The beam benders 110 are used to change the direction of the laser beam. The collimator 120 expands the laser beam which effectively changes the focused spot size. The adjustable spacer 130 is used to adjust the location of the focus point. In this particular arrangement, the spacer can be adjusted in a 1.25" range. The focus lens 14 is used to focus the laser beam on the welding site. The focus lens can be round shape or cylindrical. The round lens will generate a laser spot at the welding site, while cylindrical lens will generator a laser line at the welding site.

Figure 8:
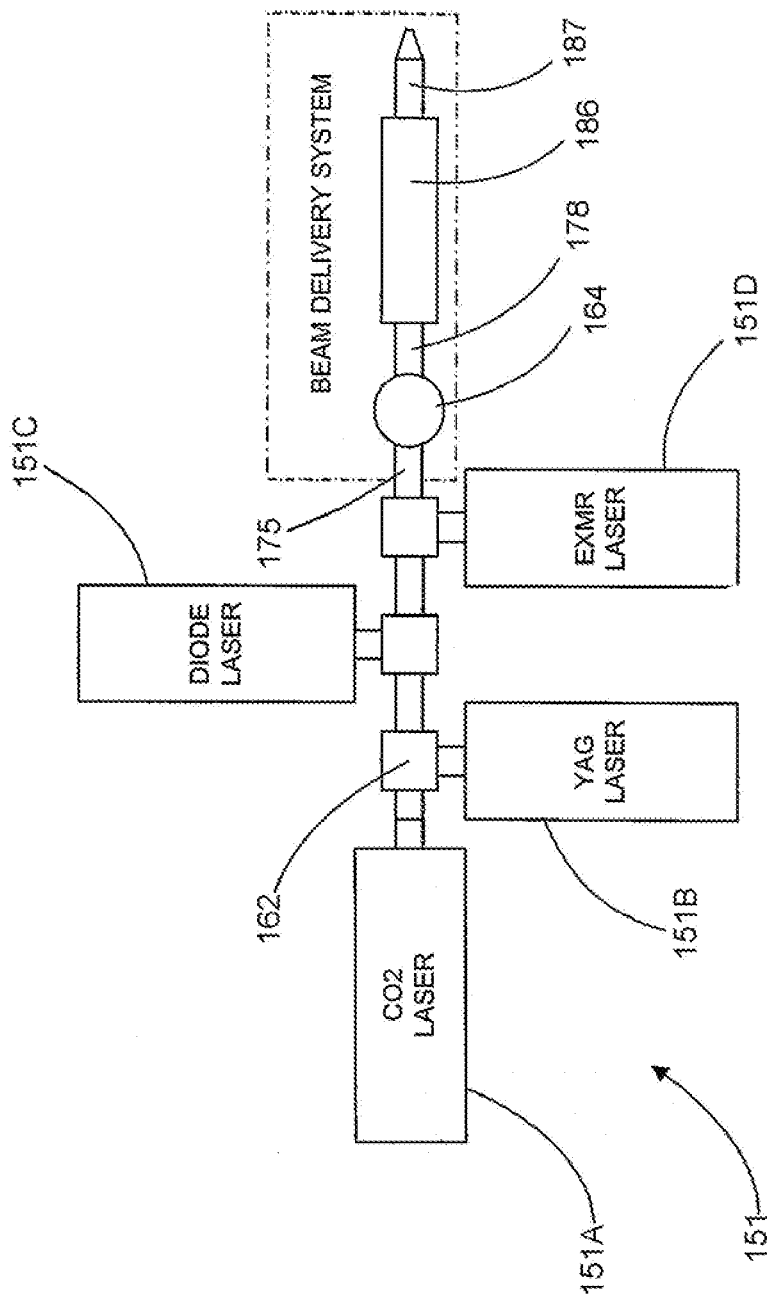
FIG. 8 is a block diagram of another laser generator for the apparatus of FIG. 1, and being constructed according to another embodiment of the invention.

Referring now to FIG. 8, there is shown a laser system 151 with multiple laser generators. The system 151 is constructed according to an embodiment of the present invention, and is similar to system of FIG. 1, except that the system 151 includes a plurality of laser generators. In this particular arrangement, a CO2 laser generator 151A, a YAG laser generator 151B, a diode laser generator 151C, and a excimer laser generator 151D are combined to form a laser energy source that provide a laser beam with multiple wave lengths. The CO2 laser generator is aligned with the main laser beam. A beam combiner generally indicated at 162 is attached to each other type of laser generator to introduce the corresponding laser beam into the main laser beam. The beam combiners are linked with beam path enclosure tubes indicated generally at 175. At the end of the multi-wave length laser generator, there may be a diode pointer (riot shown) which may be included for providing a low power visible guiding beam for sample alignment. A component 164 is a beam dump which is used to branch a certain percentage of laser power from the main laser beam to reduce the effective power. The remaining portion of the laser beam is then beam expanded and collimated through a collimator 186. It is then focused through a focus lens 187.

While particular embodiments of the present invention have been disclosed, it is to be understood that various different modifications are possible and are contemplated within the true spirit and scope of the appended claims. For example, the apparatus and method of the present invention may be implemented in a variety of different ways including techniques not employing threads.

What is claimed is:

1. A method of bonding members of a catheter, comprising:

extending a mandrel through the members of the catheter and having a free end extending from the members of the catheter;

contacting the free end of the mandrel directly with a driving means;

directly driving at a first position the free end of the mandrel extending through the members of the catheter for rotation about their axes, wherein the members of the catheter include a dilation balloon, a tubular member, and catheter tubing, and the end of the mandrel extends through the distal end of the dilation balloon;

separately driving at a second position at least one of the members of the catheter near the proximate end of the dilation balloon for rotation about their axes in synchronism with the rotation of the mandrel;

driving members and the mandrel axially at the same speed and in synchronism; and directing a main laser beam radially toward the distal end of the dilation balloon intermediate the first position and the second position to bond the distal end of the dilation balloon to the catheter tubing.

2. A method according to claim 1, further including causing the main laser beam to move axially.

3. The method of claim 1, further including generating the main laser beam using one or more laser generators selected from the group consisting of CO2 laser generators, YAG laser generators, diode laser generators, or excimer laser generators with wave length in the range of 300 nm to 15 μm to provide laser generators with different wavelengths combined to provide wide coverage of various types of polymers, polymer blends, and polymers with specially formulated coating of absorbing agents where multiple laser generators are used, further including combining laser beams using a beam combiner for each generator used to introduce their beam into the main laser beam, wherein the wave length for each laser generator being independently adjustable with the main laser beam containing only one monochromatic beam or combinations of multiple wavelengths.

4. The method of claim 3, wherein the maximum laser power generated by each laser generator is less than about 10 watts.

5. The method of claim 1, further including splitting the main laser beam into two beams with one beam traveling along a main beam path and delivered to the weld site, and the other beam branching off the main beam path and directed to a beam dump serving as a black metal block with or without cooling, to control excessive laser power being dumped, the splitting percentage of the main laser beam being in the range of about 0 to about 100%, whereby about none or about all of the laser power being dumped, the preferred percentage being between about 40% and about 95%.

6. The method of claim 1, further including expanding the waist of a laser beam coming from one of the laser generators to a larger size, the expansion ratio being in the range of between about 2 and about 10, wherein the beam expansion ratio may be adjustable.

7. The method of claim 1, further including adjusting the location of the laser focal point relative to the welding spot and the adjustment range being between 0 to 3 inches.

8. The method of claim 1, wherein the spot size at the focal point of the laser beam is adjustable in the range of 0.01 mm to 10 mm.

9. The method of claim 8, further including focusing a laser line at the focal point and the focused laser line thickness is adjustable in the range of 0.01 to 10 mm.

10. The method of claim 1, wherein at least one of the members to be bonded is made of thermoplastics.

11. The method of claim 1, wherein at least one of the members to be bonded is made of blends of thermal plastics and laser absorbing agents, the percentage of the laser absorbing agents being in the range of between about 0% and about 30%.

12. The method of claim 1, where the surfaces of at least one of the members at the bond site is coated with laser absorbing agents, the coating thickness being less than 0.010", wherein the laser absorbing agent does not contain color and absorbs laser energy in the NIR range.

13. The method of claim 1, wherein at least two of the members are pre-pressurized and held together by means of a heat shrink tubing, such heat shrink tubing being made of polyolefin or polyethylene.

14. The method of claim 13, wherein the shrink tubing is a blend of polyolefin and laser absorbing agent, the percentage of such agent being in the range of between about 0 and 30%.

* * * * *